United States Patent [19]
Chandler

[11] Patent Number: 5,648,274
[45] Date of Patent: Jul. 15, 1997

[54] COMPETITIVE IMMUNOASSAY DEVICE

[75] Inventor: Howard M. Chandler, Yarmouth, Me.

[73] Assignee: SmithKline Diagnostics, Inc., San Jose, Calif.

[21] Appl. No.: 459,466

[22] Filed: Jun. 2, 1995

Related U.S. Application Data

[63] Continuation-in-part of Ser. No. 40,430, Mar. 31, 1993, which is a continuation-in-part of Ser. No. 888,831, May 27, 1992, abandoned, which is a continuation of Ser. No. 194,793, Feb. 10, 1994, which is a continuation-in-part of Ser. No. 706,639, May 29, 1991.

[51] Int. Cl.$^6$ .................. G01N 33/558; G01N 21/00; G01N 31/22
[52] U.S. Cl. .................. 436/514; 436/518; 436/527; 436/538; 436/808; 436/805; 436/810; 422/56; 422/58; 422/61; 422/59; 435/7.1; 435/7.9; 435/7.93; 435/975
[58] Field of Search .................. 422/56, 58, 61, 422/59, 68.1, 70; 435/7.1, 7.9, 7.92, 7.93, 7.95, 975, 287.1, 287.2, 287.9, 810; 436/518, 514, 527, 538, 808, 169, 805, 810

[56] References Cited

U.S. PATENT DOCUMENTS 5,395,754  3/1995  Lambotte et al. .................. 435/607.4
5,424,220  6/1995  Goerlach-Graw et al. .................. 436/568

OTHER PUBLICATIONS

Wilchek, M. The Avidin–biotin complex in immunology, 1984; May 2; 39–43.

*Primary Examiner*—Paula K. Hutzell
*Assistant Examiner*—Bao-Thuy L. Nguyen
*Attorney, Agent, or Firm*—William H. May; Arnold Grant; Merchant & Gould

[57]  ABSTRACT

A chromatographic assay device for detection and/or determination of an analyte in a competitive immunoassay gives a semiquantitative or quantitative indication of analyte concentration in a single assay device while also giving a positive indication that flow has occurred properly through the device. In one form, the device comprises: (1) a first opposable component including a sample preparation zone and an absorber; and (2) a second opposable component including a first chromatographic medium with capture and detection zones, a second chromatographic medium with a comparison zone, and a comparison label. In another form, the second opposable component includes one chromatographic medium with capture, detection, and control zones. Test kits incorporating the devices and methods for their use are also disclosed.

28 Claims, 4 Drawing Sheets

COMPETITIVE IMMUNOASSAY DEVICE

CROSS-REFERENCES

This application is a continuation-in-part of U.S. application Ser. No. 08/040,430 by Howard M. Chandler et al., filed Mar. 31, 1993, and entitled "Assay Device," which is a continuation-in-part of U.S. application Ser. No. 07/888,831, by Howard M. Chandler, filed May 27, 1992, and also entitled "Assay Device," now abandoned in favor of a file wrapper continuation application, application Ser. No. 08/194,793, filed Feb. 10, 1994, which is a continuation-in-part of U.S. application Ser. No. 07/706,639 by Howard M. Chandler, filed May 29, 1991, and entitled "Assay Device."

BACKGROUND OF THE INVENTION

This invention is directed to test strips or assay devices for determination of characteristics of samples, unitized housings, and kits incorporating test strips and housings, and methods of determining the characteristics of samples using the test strips and housings, particularly for the performance of competitive assays.

Among the many analytical systems used for detection and/or determination of analytes, particularly analytes of biological interest, are chromatographic assay systems. Among the analytes frequently assayed with such systems are:

(1) hormones, such as human chorionic gonadotropin (hCG), frequently assayed as a marker of human pregnancy;

(2) antigens, particularly antigens specific to bacterial, viral, and protozoan pathogens, such as Streptococcus, hepatitis virus, and Giardia;

(3) antibodies, particularly antibodies induced as a result of infections with pathogens, such as antibodies to the bacterium *Helicobacter pylori* and to human immunodeficiency virus (HIV);

(4) other proteins, such as hemoglobin, frequently assayed in determinations of fecal occult blood, an early indicator of gastrointestinal disorders such as cancer;

(5) enzymes, such as aspartate aminotransferase, lactate dehydrogenase, alkaline phosphatase, and glutamate dehydrogenase, frequently assayed as indicators of physiological function and tissue damage;

(6) drugs, both therapeutic drugs, such as antibiotics, tranquilizers, and anticonvulsants, and illegal drugs of abuse, such as cocaine, heroin, and marijuana;

(7) environmental pollutants such as pesticides and aromatic hydrocarbons; and (8) vitamins.

Such chromatographic systems are frequently used by physicians and medical technicians for rapid in-office diagnosis and therapeutic monitoring of a variety of conditions and disorders. They are also increasingly used by patients themselves for at-home monitoring of such conditions and disorders.

Among the most important of such systems are the "thin layer" systems in which a solvent moves across a thin, flat absorbent medium.

Among the most important of tests that can be performed with such thin layer systems are immunoassays, which depend on the specific interaction between an antigen or hapten and a corresponding antibody. The use of immunoassays as a means of testing for the presence and/or mount of clinically important molecules has been known for some time. As early as 1956, J. M. Singer reported the use of an immune-based latex agglutination test for detecting a factor associated with rheumatoid arthritis (J. M. Singer et al., *Am. J. Med.* 22:888–892 (1956)).

Among the chromatographic techniques used in conjunction with immunoassays is a procedure known as immunochromatography. In general, this technique uses a disclosing reagent or particle that has been linked to an antibody to the molecule to be assayed, forming a conjugate. This conjugate is then mixed with a specimen and, if the molecule to be assayed is present in the specimen, the disclosing reagent-linked antibodies bind to the molecule to be assayed, thereby giving an indication that the molecule to be assayed is present. The disclosing reagent or particle can be identifiable by color, magnetic properties, radioactivity, specific reactivity with another molecule, or another physical or chemical property. The specific reactions that are employed vary with the nature of the molecule being assayed and the sample to be tested.

Immunochromatographic assays fall into two principal categories: "sandwich" and "competitive," according to the nature of the antigen-antibody complex to be detected and the sequence of reactions required to produce that complex. The antigen to be detected can itself be an antibody, such as serological assays for H. pylori-specific antibody. In such cases, the antibody to be detected can be bound to a specific antigen. Alternatively, the antigen to be detected can be detected indirectly by using a labeled second antibody that binds to the first antibody to the analyte to be detected.

In competitive immunoassays, the label is typically a labeled analyte or analyte analog which competes for binding of an antibody with any unlabeled analyte present in the sample. Competitive immunoassays are typically used for detection of analytes such as haptens, each hapten being monovalent and capable of binding only one antibody molecule. Examples of competitive immunoassay devices are those disclosed by U.S. Pat. No. 4,235,601 to Deutsch et al., U.S. Pat. No. 4,442,204 to Liotta, and U.S. Pat. No. 5,208,535 to Buechler et al., all which are incorporated herein by this reference.

Although useful, currently available chromatographic techniques using test strips have a number of drawbacks. Many samples, such as fecal samples, contain particulate material that can clog the pores of the chromatographic medium, greatly hindering the immunochromatographic process. Other samples, such as blood, contain cells and colored components that make it difficult to read the test. Still other samples, such as milk, contain fat globules or other components that can create interference. Even if the sample does not create interference, it is frequently difficult with existing chromatographic test devices to apply the sample to the chromatographic medium so that the sample front moves uniformly through the chromatographic medium to insure that the sample reaches the area where binding is to occur in a uniform, straight-line manner.

Other problems exist with currently-available test strips because of the nature of the sample to be assayed or the assay to be carried out. With such devices, it is impractical to perform washing steps which are frequently desirable to improve sensitivity and to reduce to background. Also, it is difficult, and in many cases impossible, to carry out preincubation steps within the device. Additionally, there is a need for an immunochromatographic assay device that can carry out a broad range of separations, such as a separation of fat from milk or the separation of organic chemicals such as the separation of benzene from toluene.

Sample preparation and waste generation are responsible for other problems with currently available devices and techniques for immunochromatography. The increased prevalence of diseases spread by infected blood and blood fractions, as well as other bodily secretions, such as AIDS and hepatitis, has exacerbated these problems. It is rarely possible to apply a sample (such as feces) or a sampling device (such as a throat swab) directly to the chromatographic medium. Several extraction and pretreatment reactions are usually required before the sample can be applied to the chromatographic medium. These reactions are typically carried out by the physician or technician performing the test in several small vessels, such as test tubes, or microfuge tubes, requiring the use of transfer devices, such as pipettes. Each of these devices is then contaminated and must be disposed of using special precautions so that workers or people who may inadvertently come into contact with the waste do not become contaminated.

Additionally, currently available test devices, although useful, are generally not suited to give a semi-quantitative or quantitative indication of the concentration of an analyte present in a test sample, particularly for competitive immunoassays. Typically, the obtaining of such a quantitative or semi-quantitative indication requires the use of more than one test device, such as for calibration. The use of more than one test device requires a greater expenditure of time and material and also increases the possibility that a mistake may be made during the performance of the assay. In particular, with possibly contaminated samples, there may be concern that, inadvertently, a device thought to contain only a control actually contains a sample that may contain an infectious agent. Thus, it would be preferable to be able to determine a quantitative or semi-quantitative indication of analyte concentration in one assay device without the use of a separate assay device as a control or for calibration.

There is further need for an assay device that gives a positive indication that the test has been performed correctly and that flow has occurred properly within the chromatographic assay device.

Accordingly, there is a need for an improved assay device capable of handling a broad range of chromatographic assays. Such a device should be able to handle all types of immunoassays, particularly competitive immunoassays, as well as other types of assays using chromatography. Such a device should be capable of receiving a possibly contaminated sample or a sample preparation device directly so as to eliminate the need for extraction vessels and transfer devices. Such a device, particularly in the form of a test strip, should also be capable of performing immunochromatographic assays on colored samples or samples containing particulates without interference and should be able to deliver the sample to the chromatographic medium uniformly and evenly to improve accuracy and precision of the tests. Additionally, such an improved test strip should be capable of carrying out semi-quantitative or quantitative indications of analyte concentration in a single assay device without the need for additional control assay devices, and should give a positive indication that flow within the device has occurred properly and that the assay has operated correctly.

SUMMARY

I have developed an assay device that meets these needs, and performs semiquantitative or quantitative determinations of analyte concentration in a single assay device without requiring additional control assay devices. The assay device of the present invention also provides a positive indication of proper performance of the assay. The device can perform competitive immunoassays for a wide variety of analytes, particularly haptens.

One aspect of the present invention is a competitive immunoassay device comprising:

(1) a first opposable component including:
  (a) a sample preparation zone including a labeled specific binding partner for an analyte conjugated to a first member of an auxiliary specific binding pair in resolubilizable form; and
  (b) an absorber for absorbing fluid therein separated from the sample preparation zone on the first opposable component; and (2) a second opposable component hingedly attachable to the first opposable component including:
  (a) a first chromatographic medium having first and second ends and including thereon:
    (i) a first zone of immobilized analyte or analog thereof bound to the first chromatographic medium; and
    (ii) a second zone of an immobilized molecule that is a second member of the auxiliary specific binding pair with specific affinity for the first member bound to the first chromatographic medium;
  (b) a second chromatographic medium having a first end and a second end and including thereon a comparison zone containing a known quantity of the analyte or analog thereof immobilized to the comparison zone; and
  (c) a comparison label zone including therein a labeled specific binding partner to the analyte or analog thereof in resolubilizable form in operable contact with the second chromatographic medium.

When the first and second opposable components are brought into opposition from a position in which they are not in opposition, the sample preparation zone comes into operable contact with the first end of the first chromatographic medium to apply the sample and the labeled specific binding partner for the analyte conjugated to biotin to the first chromatographic medium. The absorber also comes into operable contact with the second end of the first chromatographic medium and the second end of the second chromatographic medium to draw fluid through the first and second chromatographic medium from their first end to their second end so that the device gives a detectable indication of the presence of an analyte at a quantity greater than a predetermined amount by a comparison of the intensity of the label bound at the detection zone of the first chromatographic medium and at the comparison zone of the second chromatographic medium.

Preferably, the sample preparation zone on the first opposable component further includes a second labeled specific binding partner that binds a molecule not substantially cross-reactive with the analyte in resolubilizable form, and the first chromatographic medium further includes a flow control indicator including a molecule binding the second labeled specific binding partner so that the flow control indicator gives a positive indication that flow has occurred through the first chromatographic medium.

Preferably, the label of both the labeled specific binding partner for the analyte conjugated to the first member of the auxiliary specific binding pair and the labeled specific binding partner to the analyte in the comparison label zone are visibly detectable labels. Preferably, the labeled specific binding partner to the analyte conjugated to the first member of the auxiliary specific binding pair at the sample preparation zone and the labeled specific binding partner to the analyte at the comparison label zone are the same label.

Preferably, the first member of the auxiliary specific binding pair is biotin. When the first member of the auxiliary specific binding pair is biotin, the second member of the auxiliary specific binding pair is preferably streptavidin.

In one typical embodiment of this device, the analyte is a β-lactam antibiotic, the first zone of immobilized analyte or analog thereof is 7-aminocephalosporanic acid conjugated to immunoglobulin, and the labeled specific binding partner for the analyte conjugated to the first member of the auxiliary specific binding pair is biotinylated penicillin binding protein.

In another typical embodiment of this device, the analyte is an antibiotic selected from the group consisting of gentamycin, sulfamethazine, and tetracycline, the first zone of immobilized analyte or analog thereof is analyte covalently conjugated to immunoglobulin, and the labeled specific binding partner for the analyte conjugated to the fist member of the auxiliary specific binding pair is a biotinylated anti-analyte antibody.

Another aspect of the present invention is a test kit for detection and/or determination of an analyte comprising, packaged in separate containers:

(1) the immunoassay device described above; and
(2) a liquid for resolubilizing the labeled specific binding partner to the analyte or analog thereof in the comparison label zone.

Another aspect of the present invention is a method for detecting and/or determining an analyte in a test sample by a competitive immunoassay comprising the steps of:

(1) adding a test sample to the sample preparation zone of the competitive immunoassay device described above;
(2) allowing the test sample to resolubilize the labeled specific binding partner for the analyte conjugated to the first member of the auxiliary specific binding pair;
(3) adding a liquid to the comparison label zone to resolubilize the labeled specific binding partner to the analyte or analog thereof;
(4) bringing the first and second opposable components into opposition from a position in which they are not in opposition to bring the absorber on the first opposable component into operable contact with the second end of the first chromatographic medium and the second end of the second chromatographic medium and to bring the sample preparation zone into operable contact with the first end of the first chromatographic medium;
(5) allowing the sample and the labeled specific binding partner for the analyte conjugated to the first member of the auxiliary specific binding pair to flow through the first chromatographic medium and the labeled specific binding partner to the analyte or analog thereof to flow through the second chromatographic medium so that, if analyte is present in the test sample, the labeled specific binding partner to the analyte conjugated to the first member of the auxiliary specific binding pair binds to the detection zone on the first chromatographic medium and so that the labeled specific binding partner to the analyte or analog thereof binds to the comparison zone on the second chromatographic medium; and
(6) comparing the intensity of label at the detection zone on the first chromatographic medium and at the comparison zone on the second chromatographic medium to detect and/or determine the analyte in the test sample.

Yet another aspect of the present invention is another version of a competitive immunoassay device that uses a single chromatographic medium to provide both detection and control functions. This version comprises:

(1) a first opposable component including:
   (a) a sample preparation zone including:
      (i) a labeled specific binding partner for an analyte conjugated to a first member of an auxiliary specific binding pair in resolubilizable form; and
      (ii) a predetermined quantity of the analyte or an analog thereof covalently bound to a labeled specific binding partner for a molecule that does not substantially cross-react with the analyte in resolubilizable form; and
   (b) an absorber separated from the sample preparation zone; and
(2) a second opposable component including a chromatographic medium with first and second ends, the chromatographic medium including thereon in discrete, nonoverlapping zones:
   (a) a first, capture, zone of immobilized analyte or analog thereof bound to the chromatographic medium;
   (b) a second, detection, zone including an immobilized molecule that is a second member of the auxiliary specific binding pair with specific affinity for the first member bound to the chromatographic medium; and
   (c) a third, control, zone including an immobilized molecule capable of being specifically bound to the labeled specific binding partner covalently conjugated to the analyte or analog thereof bound to the chromatographic medium.

In this embodiment of an assay device according to the present invention, the first and second opposable components are configured so that bringing the first and second opposable components into opposition from a position in which they are not in opposition causes the absorber to come into operable contact with the second end of the chromatographic medium and causes the sample preparation zone to come into contact with the first end of the chromatographic medium so that the test sample, the resolubilized labeled specific binding partner for the analyte conjugated to the first member of the auxiliary specific binding pair, and the predetermined quantity of the analyte or analog thereof covalently bound to a labeled specific binding partner flow through the chromatographic medium from the first end to the second end. As a result, the device gives a detectable indication of the presence of an analyte at a quantity greater than a predetermined amount by a comparison of the intensity of the label bound at the detection zone and at the control zone of the second chromatographic medium.

Typically, the label of the labeled specific binding partner for the analyte conjugated to the first member of the auxiliary specific binding pair and the label of the labeled specific binding partner for the molecule that does not substantially cross-react with the analyte are both visually detectable labels.

In one typical embodiment of this device, in which the first member of the auxiliary specific binding pair is biotin and the second member of the auxiliary specific binding pair is streptavidin, the analyte is a β-lactam antibiotic, the labeled specific binding partner for the analyte conjugated to the first member of the auxiliary specific binding pair is a penicillin binding protein, the immobilized analyte or analog thereof bound at the capture zone on the chromatographic medium is 7-aminocephalosporanic acid covalently conjugated to immunoglobulin G, the labeled specific binding partner for a molecule that does not substantially cross-react with the analyte is an anti-rabbit immunoglobulin G antibody, and the immobilized molecule bound at the control zone on the chromatographic medium is rabbit immunoglobulin G.

Alternatively, the analyte can be an antibiotic selected from the group consisting of gentamycin, sulfamethazine, and tetracycline, the labeled specific binding partner for the analyte conjugated to the first member of the auxiliary specific binding pair can be an anti-analyte antibody, the labeled specific binding partner for a molecule that does not substantially cross-react with the analyte can be anti-rabbit immunoglobulin G, the immobilized analyte or analog thereof bound at the capture zone on the chromatographic medium can be the analyte covalently bound to immunoglobulin G of a species other than the species other than rabbit, and the immobilized molecule bound at the control zone can be rabbit immunoglobulin G.

Another aspect of the present invention is a method for detecting and/or determining an analyte in a test sample by a competitive immunoassay comprising the steps of:

(1) applying the sample to the sample preparation zone of the single-chromatographic medium competitive immunoassay device described above;

(2) allowing the sample applied to the sample preparation zone to resolubilize the labeled specific binding partner for the analyte conjugated to the first member of the auxiliary specific binding pair and the predetermined quantity of the analyte or analog thereof covalently bound to the labeled specific binding partner for the molecule that does not substantially cross-react with the analyte;

(3) bringing the first and second opposable components into opposition from a position in which they are not in opposition so that the absorber is brought into operable contact with the second end of the chromatographic medium and so that the sample preparation zone is brought into operable contact with the first end of the chromatographic medium;

(4) allowing the sample, the labeled specific binding partner for the sample, and the analyte or analog thereof covalently bound to the labeled specific binding partner for the molecule that does not substantially cross-react with the analyte to migrate through at least a portion of the chromatographic medium including the detection zone and the control zone; and (5) detecting and/or determining the concentration of analyte in the test sample by comparing the intensities of label at the detection zone and the control zone of the chromatographic medium.

Yet another aspect of the present invention is multiplex assay devices that can perform more than one assay simultaneously. One version of such a multiplex assay device comprises:

(1) a first opposable component including:
   (a) a plurality of sample preparation zones, each sample preparation zone including a labeled specific binding partner for an analyte conjugated to a first member of an auxiliary specific binding pair in resolubilizable form; and
   (b) an absorber for absorbing fluid therein separated from the sample preparation zones on the first opposable component; and (2) a second opposable component hingedly attachable to the first opposable component including:
   (a) a plurality of first chromatographic media, one for each sample preparation zone, each first chromatographic medium having first and second ends and including thereon:
      (i) a first zone of an immobilized analyte or analog thereof bound to the first chromatographic medium; and
      (ii) a second zone of an immobilized molecule that is a second member of the auxiliary specific binding pair with specific affinity for the first member bound to the first chromatographic medium;
   (b) a plurality of second chromatographic media, one for each sample preparation zone, each second chromatographic medium having a first end and a second end and including thereon a comparison zone containing a known quantity of an analyte or analog thereof immobilized to the comparison zone; and
   (c) a plurality of comparison label zones, one for each second chromatographic medium, each comparison label zone including therein a labeled specific binding partner to the analyte or analog thereof in resolubilizable form in operable contact with the second chromatographic medium.

In this version of a multiplex assay device according to the present invention, when the first and second opposable components are brought into opposition from a position in which they are not in opposition, the sample preparation zones come into operable contact with the first end of each first chromatographic medium to apply the sample and the labeled specific binding partner for the analyte conjugated to the first member of the auxiliary specific binding pair to each first chromatographic medium, and the absorber comes into operable contact with the second end of each first chromatographic medium and the second end of each second chromatographic medium to draw fluid through the first and second chromatographic media from their first ends to their second ends. As a result, the device gives a detectable indication of the presence of an analyte in each first and second chromatographic medium at a quantity greater than a predetermined amount by a comparison of the intensity of the label bound at the detection zone of each first chromatographic medium and at the comparison zone of each second chromatographic medium.

A test kit incorporating this version of a multiplex assay device according to the present invention comprises:

(1) the immunoassay device; and
(2) a liquid for resolubilizing the labeled specific binding partner to the analyte or analog thereof in each comparison label zone.

A method for using this multiplex assay device comprises:

(1) adding a test sample to at least one of the sample preparation zones of the multiplex assay device;

(2) allowing the at least one test sample to resolubilize the labeled specific binding partners for the analyte conjugated to the first member of the auxiliary specific binding partner;

(3) adding a liquid to at least one of the comparison label zones to resolubilize the labeled specific binding partner to the analyte or analog thereof;

(4) bringing the first and second opposable components into opposition from a position in which they are not in opposition to bring the absorber on the first opposable component into operable contact with the second end of the first chromatographic media and the second end of the second chromatographic media and to bring the sample preparation zones into operable contact with the first ends of the first chromatographic media;

(5) allowing the at least one sample and the labeled specific binding partner for the analyte conjugated to the first member of the auxiliary specific binding pair to flow through the first chromatographic media and the labeled specific binding partner to the analyte or analog thereof to flow through the second chromatographic media so that, if analyte is present in any test sample, the labeled specific binding partner to the analyte conjugated to biotin binds to the detection zone on the corresponding first chromatographic medium and so that the labeled specific binding partner binds to the comparison zone on the corresponding second chromatographic medium; and (6) comparing the intensity of label at the detection zone on each first chromatographic medium and at the comparison zone on each second chromatographic medium to detect and/or determine the analyte in each test sample.

Another version of a multiplex assay device according to the present invention is based on the version of the device using a single chromatographic medium and comprises:

(1) a first opposable component including:
   (a) a plurality of sample preparation zones, each sample preparation zone including:
      (i) a labeled specific binding partner for an analyte conjugated to a first member of an auxiliary specific binding pair in resolubilizable form; and
      (ii) a predetermined quantity of an analyte or an analog thereof covalently bound to a labeled specific binding partner for a molecule that does not substantially cross-react with the analyte in resolubilizable form; and
   (b) an absorber separated from the sample preparation zones; and (2) a second opposable component including a plurality of chromatographic media with first and second ends, each chromatographic medium including thereon in discrete, nonoverlapping zones:
   (a) a first, capture, zone of immobilized analyte or analog thereof bound to the chromatographic medium;
   (b) a second, detection, zone including an immobilized molecule that is a second member of the auxiliary specific binding pair with specific affinity for the first member bound to the chromatographic medium; and
   (c) a third, control, zone including an immobilized molecule capable of being specifically bound to the labeled specific binding partner covalently conjugated to the analyte or analog thereof bound to the chromatographic medium.

In this version of a multiplex assay device according to the present invention, the first and second opposable components are configured so that bringing the first and second opposable components into opposition from a position in which they are not in opposition causes the absorber to come into operable contact with the second end of each chromatographic medium and causes the sample preparation zones to come into contact with the first end of each chromatographic medium so that the test samples, the resolubilized labeled specific binding partners for the analyte conjugated to the first member of the auxiliary specific binding pair and the predetermined quantities of the analyte or analog thereof covalently bound to a labeled specific binding partner flow through each chromatographic medium from the first end to the second end.

A method for using this version of the multiplex assay device comprises:

(1) applying a sample to at least one of the sample preparation zones of the multiplex assay device;

(2) allowing the at least one sample applied to the sample preparation zones to resolubilize the labeled specific binding partner for the analyte conjugated to the first member of the auxiliary specific binding pair and the predetermined quantity of the analyte or analog thereof covalently bound to the labeled specific binding partner for the molecule that does not substantially cross-react with the analyte;

(3) bringing the first and second opposable components into opposition from a position in which they are not in opposition so that the absorber is brought into operable contact with the second end of each chromatographic medium and so that each sample preparation zone is brought into operable contact with the first end of each chromatographic medium;

(4) allowing the at least one sample, the labeled specific binding partner for the sample, and the analyte or analog thereof covalently bound to the labeled specific binding partner for the molecule that does not substantially cross-react with the analyte to migrate through at least a portion of each chromatographic medium including the detection zone and the control zone; and (5) detecting and/or determining the concentration of analyte in each test sample by comparing the intensities of label at the detection zone and the control zone of each chromatographic medium.

BRIEF DESCRIPTION OF THE DRAWINGS

These and other features, aspects, and advantages of the present invention will become better understood with reference to the following description, appended claims, and accompanying drawings where:

DESCRIPTION

Definitions

Figure 1:
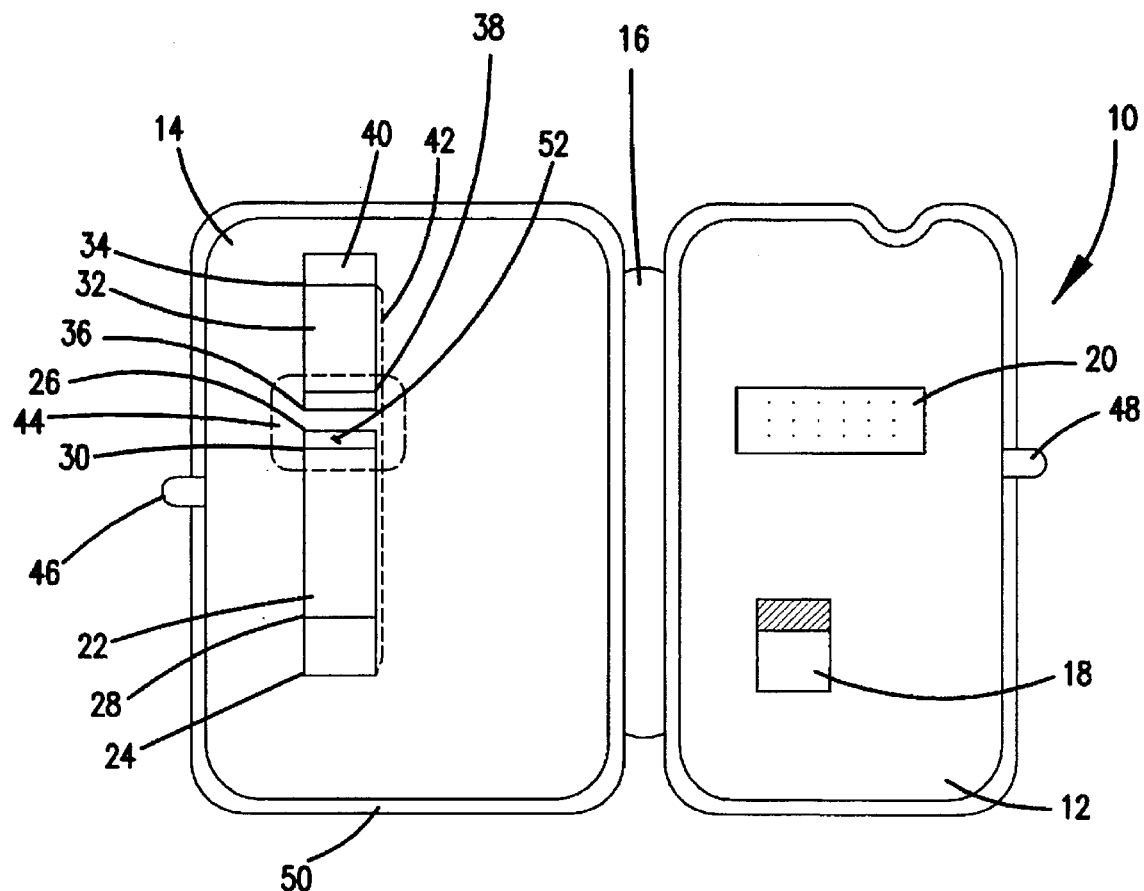
FIG. 1 is a drawing of a first embodiment of a competitive immunoassay device according to the present invention employing two chromatographic media.

In the context of this disclosure, the following terms are defined as follows unless otherwise indicated:

Specific Binding Partner: A member of a pair of molecules that interact by means of specific non-covalent interactions that depend on the three-dimensional structures of the molecules involved. Typical pairs of specific binding partners include antigen-antibody, hapten-antibody, hormone-receptor, nucleic acid strand-complementary nucleic acid strand, substrate-enzyme, β-lactam antibiotic-penicillin binding protein, inhibitor-enzyme, carbohydrate-lectin, biotin-avidin, and virus-cellular receptor.

Immunoassay: As used herein, the term "immunoassay" includes assays involving at least one specific binding partner as defined above and is not necessarily limited to assays in which the specific binding partner is an antibody unless such a limitation is specified.

Operable Contact: Two solid components are in operable contact when they are in contact, either directly or indirectly, in such a manner that a liquid, typically an aqueous liquid, can flow from one of the two components to the other Substantially uninterruptedly, by capillarity or otherwise. "Direct contact" means that the two elements are in physical contact, such as edge-to-edge or front-to-back. Typically, when two components are in direct contact, they are overlapped with an overlap of about 0.5 to about 3 mm. However, the components can be placed with abutting edges. "Indirect contact" means that the two elements are not in physical contact, but are bridged by one or more conductors.

Analyte: The term "analyte" includes both the actual molecule to be assayed and analogues and derivatives thereof when such analogues and derivatives bind another molecule used in the assay in a manner substantially equivalent to that of the analyte itself in terms of affinity and cross-reactivity.

Antibody: The term "antibody" includes both intact antibody molecules of the appropriate specificity and antibody fragments (including Fab, F(ab'), and F(ab')$_2$ fragments) as well as chemically modified intact antibody molecules and antibody fragments, including hybrid antibodies assembled by in vitro reassociation of subunits.

Auxiliary Specific Binding Pair: The term "auxiliary specific binding pair" refers to a pair of molecules that are specific binding partners of each other, as that term is defined above, with neither member of the pair having specific binding affinity for any other molecule participating in the assay performed by assay devices according to the present invention. An example of an auxiliary specific binding pair is biotin-avidin.

I. CHROMATOGRAPHIC ASSAY DEVICES

One aspect of the present invention comprises chromatographic assay devices particularly useful for the assay of analytes and biological samples, particularly by competitive immunoassays. These devices are suitable for the direct application of biological samples, without preliminary extraction steps, and are constructed so as to minimize interference with assay results caused by particulates or colored samples.

The device has at least two substantially planar opposable components. One of the substantially planar components has on its surface a chromatographic medium.

The device also has means for opposing the opposable components and applying pressure thereto. Typically, bringing the opposable components into opposition is performed by direct manual closure. The pressure applied is sufficient to transfer fluid from one opposable component to another opposable component in a direction substantially normal to the opposable components so that the sample is applied to the chromatographic medium for detection and/or determination of the analyte thereon. The pressure also drives fluid through the chromatographic medium to accelerate the process of chromatography, giving a detectable result in less time. Additionally, the pressure makes possible the performance of steps, such as extraction steps, in the device, and can be used to remove excess fluid from the chromatographic medium by absorbers to reduce the background of the assays. The pressure is generated by placing the opposable components into opposition and maintained by holding the components in opposition by engagers such as locks or clasps. The pressure is calibrated to be optimum for a particular assay, and can vary depending upon the construction of the device, the material used in the chromatographic medium, the volume and nature of the sample, the nature of the specific binding partner and label, and other factors.

Assay devices according to the present invention perform immunoassays without requiring the application of additional liquid to the chromatographic medium of the devices once the sample is applied. This avoids dilution of the sample or the specific binding partners and preserves maximum sensitivity of the assays.

Typically, devices according to the present invention are constructed for the performance of a competitive immunoassay. However, devices can be constructed by similar principles for the performance of other types of immunoassays and are within the scope of the invention.

In a device suitable for the performance of a competitive immunoassay, the chromatographic medium has incorporated thereon a detection zone of a specific binding partner for a labeled component. The labeled component is a first member of an auxiliary specific binding pair, and the detection zone includes a second member of the auxiliary specific binding pair.

In one particularly preferable alternative employing an auxiliary specific binding pair, the detection zone is an immobilized molecule with specific affinity for biotin, and the assay includes a labeled specific binding partner for an analyte conjugated to biotin. The immobilized molecule with specific affinity for biotin is typically streptavidin, but can also be avidin or an anti-biotin antibody.

The term "biotin", as used herein, includes not only biotin itself, but also derivatives of biotin in which the binding between the derivative of biotin and its specific binding partner is substantially equivalent to that between biotin itself and the specific binding partner. These derivatives include iminobiotin and biotin covalently conjugated to a spacer, such as $\epsilon$-caproamidobiotin. Other derivatives of biotin, such as those incorporating spacers of varying lengths, can also be used.

The detection zone is substantially smaller than the chromatographic medium. It typically extends the entire width of the chromatographic medium, but can be confined to a spot that is smaller than the entire width of the chromatographic medium.

Typically, detection and/or determination of the analyte after the performance of the assay occurs by use of a visually detectable labeled component. The labeled component is preferably either the analyte or an analog thereof linked to a visually detectable label, or a specific binding partner for the analyte linked to a visually detectable label. In the arrangements described below for competitive immunoassays, the labeled component is typically a labeled specific binding partner for an analyte conjugated to a first member of an auxiliary specific binding pair. Preferably, the first member of the auxiliary specific binding pair is biotin. When the first member of the auxiliary specific binding pair is biotin, the second member of the auxiliary specific binding pair is preferably streptavidin.

Ligand analogs, including analyte analogs, are well known in the art and are described, for example, in U.S. Pat. No. 3,817,837 to Rubenstein et al., incorporated herein by this reference. Analyte analogs can be conjugated to a larger protein, such as immunoglobulin that is unreactive in the immunoassay, through a linker. The length of the linker can be selected for optimal performance in the assay performed by the device. Various linking reactions can be used to synthesize the analyte analogs, depending on the functional groups available. Such linking reactions are described, for example, in U.S. Pat. No. 3,817,837 to Rubenstein et al.

Assay devices according to the present invention can be constructed for the performance of more than one assay simultaneously. In such devices, one of the substantially planar components has at least two separate and non-contacting chromatographic media thereon. These are described further below.

A. Elements Common to Devices According to the Present Invention

A number of elements are common to assay devices according to the present invention and are discussed here for convenience.

1. The Chromatographic Medium

The chromatographic medium is a strip. Typically, the strip is substantially planar, although this is not required in all applications. It is typically rectangular, having first and second ends and first and second surfaces. Throughout this description, the term "first end" refers to the end at which liquid is first applied to the chromatographic medium and the term "second end" applies to the opposite end of the chromatographic medium. The liquid applied at or near the first end of the chromatographic medium can be, but is not necessarily, a sample or a treated sample. The chromatographic medium is composed of material suitable as a medium for thin layer chromatography of analyte and analyte-antibody conjugates, such as nitrocellulose, nylon, rayon, cellulose, paper, or silica. The chromatographic medium can be pretreated or modified as needed.

The reagent located in the detection zone is immobilized on the chromatographic medium in such a way that it is stabilized against diffusive movement. The reagent can be bound to the chromatographic medium by either covalent or non-covalent means; both are well-known in the art and need not be described further here in detail. If the chromatographic medium is nitrocellulose, the reagent in the detection zone can be bound by a hydrophobic interaction.

The binding of reagents to solid phases is described, for example, in P. Tijssen, "Practice and Theory of Enzyme Immunoassays" (Elsevier, Amsterdam, 1985), pp. 297–328.

Typically, the chromatographic medium is translucent, so that colored zones appearing on it can be viewed from either side.

2. Absorbers

In a number of devices according to the present invention, absorbers are in operable contact with one or both ends of the chromatographic medium. The absorbers can be made of any bibulous material that holds a liquid, typically an aqueous liquid, sufficiently so that liquid can be drawn through the chromatographic medium and accumulated in the absorber. Typical materials include, but are not limited to, filter paper.

3. Other Fluid-Carrying Elements

As described below, in particular devices according to the present invention, other fluid-carrying elements can be employed as sample preparation zones, applicators, and/or conductors. These elements are prepared of hydrophilic media that pass liquids, typically aqueous liquids, without substantially absorbing them. Such materials are well-known in the art.

In some cases, these elements can have incorporated therein a component in dry form that can be resolubilized by addition of a liquid, typically an aqueous liquid, to the element. This component can be a labeled component or another component of the reaction.

4. Opposable Components

Many of the embodiments of the assay device according to the present invention comprise two opposable components. The bodies of the opposable components are preferably made of laminated cardboard that is sufficiently impervious to moisture to contain the liquids involved in the performance of the assay carried out by the device for the period of time during which the assay is carried out.

Other cellulose-based materials, such as paperboard or solid bleached sulfite (SBS), can also be used. Alternatively, the bodies of the opposable components can be made of plastic that is impermeable to moisture. A suitable plastic is a polycarbonate plastic such as Lexan™.

The opposable components are typically joined by a hinge, preferably made of a material impermeable to liquids, including aqueous liquids, such as a plastic that can be compatibly joined with or is the same as the material used for the first and second opposable components.

5. Labeled Components

For assay devices according to the present invention intended to perform a competitive immunoassay, the labeled component is typically a labeled specific binding partner to the analyte that is also conjugated to biotin. However, other labelling arrangements can be used.

The label is preferably a visually detectable label, such as a colloidal metal label. Preferably, the colloidal metal label is gold, silver, bronze, iron, or tin; most preferably, it is gold. The preparation of gold-labeled antibodies and antigens is described in J. DeMey, "The Preparation and Use of Gold Probes", in *Immunocytochemistry: Modern Methods and Applications* (J. M. Polak & S. Van Noorden, eds., Wright, Bristol, England, 1986), Ch. 8, pp. 115–145; other references to the preparation of such labeled antibodies and antigens are known in the art. Antibodies labeled with colloidal gold are commercially available, such as from Sigma Chemical Company, St. Louis, Mo. Alternatively, other colloidal labels, such as a colloidal sulfur label or a dye-silica label, can also be used. In a less preferred alternative, the visually detectable label can be a colloidal latex label. It is also possible to use other labels, such as a radioactive label, a fluorescent label, a chemiluminescent label, a bioluminescent label, or an enzyme label.

B. Assay Devices for Competitive Immunoassays

1. Assay Device for Competitive Immunoassays with Two Chromatographic Media

One embodiment of the present invention suitable for performing competitive immunoassays uses two separate chromatographic media on a single opposable component. One of these chromatographic media is used to perform the immunoassay, while the other provides a comparison using a known quantity of analyte in order to determine whether or not the analyte is present in the test sample at a concentration higher than a predetermined concentration.

In general, this immunoassay device comprises:

(1) a first opposable component including:
   (a) a sample preparation zone including a labeled specific binding partner for an analyte conjugated to a first member of an auxiliary specific binding pair in resolubilizable form; and
   (b) an absorber for absorbing fluid therein separated from the sample preparation zone on the first opposable component; and (2) a second opposable component hingedly attachable to the first opposable component including:
   (a) a first chromatographic medium having first and second ends and including thereon:
     (i) a first zone of immobilized analyte or analog thereof bound to the first chromatographic medium; and
     (ii) a second zone of an immobilized molecule that is a second member of the auxiliary specific binding pair with specific affinity for the first member bound to the first chromatographic medium;
   (b) a second chromatographic medium having a first end and a second end and including thereon a comparison zone containing a known quantity of the analyte or analog thereof immobilized to the comparison zone; and (c) a comparison label zone including therein a labeled specific binding partner to the analyte or analog thereof in resolubilizable form in operable contact with the second chromatographic medium.

When the first and second opposable components are brought into opposition from a position in which they are not in opposition, the sample preparation zone comes into operable contact with the first end of the first chromatographic medium to apply the sample and the labeled specific binding partner for the analyte conjugated to biotin to the first chromatographic medium, and the absorber comes into operable contact with the second end of the first chromatographic medium and the second end of the second chromatographic medium to draw fluid through the first and second chromatographic medium from their first end to their second end. The device gives a detectable indication of the presence of an analyte at a quantity greater than a predetermined amount by a comparison of the intensity of the label bound at the detection zone of the first chromatographic medium and at the comparison zone of the second chromatographic medium.

This device is shown in FIG. 1.

The device 10 includes a first opposable component 12 and a second opposable component 14, attached by a hinge 16. The first opposable component 12 comprises a sample preparation zone 18. The sample preparation zone 18 includes a labeled specific binding partner for an analyte conjugated to a first member of an auxiliary specific binding pair in a form that can be resolubilized by the addition of a liquid to the sample preparation zone 18. The first opposable component 12 further includes an absorber 20 for absorbing fluid. The absorber 20 is separated from the sample preparation zone 18 on the first opposable component 12.

The second opposable component 14 includes a first chromatographic medium 22. The first chromatographic medium 22 has a first end 24 and a second end 26. The first chromatographic medium 22 includes thereon: (i) a first zone 28 of immobilized analyte or analog thereof bound to the first chromatographic medium 22 and (ii) a second zone 30 of an immobilized molecule that is a second member of the auxiliary specific binding pair bound to the first chromatographic medium 22. When the first member of the auxiliary specific binding pair is biotin, the immobilized molecule with specific affinity for biotin is typically streptavidin but can alternatively be avidin or an anti-biotin antibody.

The second opposable component 14 also includes a second chromatographic medium 32. The second chromatographic medium 32 has a first end 34 and a second end 36 and includes thereon a comparison zone 38 containing a known quantity of the analyte or an analog thereof immobilized to the comparison zone 38. The second opposable component 14 further includes a comparison label zone 40 including therein a labeled specific binding partner to the analyte or analog thereof in a form that can be resolubilized by the addition of a liquid, typically an aqueous liquid, to the comparison label zone 40. The comparison label zone 40 is in operable contact with the second chromatographic medium 32 so that, when the labeled specific binding partner to the analyte or analog is resolubilized, it diffuses into the second chromatographic medium 32. The first and second chromatographic media 22 and 32 can be backed by a backing 42, which can be a plastic such as polycarbonate (Lexan) or other impermeable plastic.

When the first and second opposable components 12 and 14 are brought into opposition from a position in which they are not in opposition, the sample preparation zone 18 comes into operable contact with the first end 24 of the first chromatographic medium 22 to apply the sample and the labeled specific binding partner for the analyte conjugated to the first member of the auxiliary specific binding pair to the first chromatographic medium 22. The absorber 20 on the first opposable component 12 comes into operable contact with both the second end 26 of the first chromatographic medium 22 and the second end 36 of the second chromatographic medium 32 to draw fluid through the first and second chromatographic media 22 and 32 from their first ends 24 and 34 to their second ends 26 and 36. The absorber 20 is large enough so that it can absorb the fluid from both the first chromatographic medium 22 and the second chromatographic medium 32.

The first opposable component 12 can have an aperture 44 therein to view the second zone 30 on the first chromatographic medium 24 and the comparison zone 38 on the second chromatographic medium 32. The device 10 can also include engagers such as locks 46 and 48 to hold the first and second opposable components 12 and 14 in opposition and a gasket 50 to prevent the escape of fluids from the device.

Preferably, the first chromatographic medium 22 on the second opposable component 14 further includes a flow control indicator 52. The flow control indicator 52 is located near the second end 26 of the first chromatographic medium 22. When a flow control indicator 52 is used, the sample preparation zone 18 on the first opposable component 12 further includes a second labeled specific binding partner that binds a molecule not substantially cross-reactive with the analyte in a form that can be resolubilized by the addition of a liquid, typically an aqueous liquid, to the sample preparation zone. The flow control indicator 52 includes a molecule binding the second labeled specific binding partner so that the flow control indicator 52 gives a positive indication the flow has occurred through the first chromatographic medium 22.

In carrying out the assay with the assay device 10, a sample is added to the sample preparation zone 18 on the first opposable component 12. The sample resolubilizes the labeled specific binding partner for the analyte conjugated to the first member of the auxiliary specific binding pair, and also the second labeled specific binding partner that binds the molecule not substantially cross-reactive with the analyte, to give the indication of flow control. The assay device 10 is then allowed to incubate for a predetermined period of time, typically 1 minute to 10 minutes. This incubation can be performed at room temperature; alternatively, the assay device 10, or the first opposable component 12 of the assay device 10, can be placed in an incubator that raises the temperature to a temperature higher than room temperature, such as 30° C. or 37° C., for a faster assay. Even higher temperatures can be used if such temperatures would not result in inactivation or denaturation of the antibodies or other specific binding partners.

After the incubation, a buffer or other aqueous reagent is applied to the comparison label zone 40 on the second opposable component 14. The resolubilized labeled specific binding partner to the analyte or analog thereof is then allowed to migrate through the second chromatographic medium 32 from its first end 34 toward its second end 36.

The assay device 10 is then closed, bringing the first and second opposable components 12 and 14 into opposition, and applying the resolubilized labeled specific binding partner for the analyte conjugated to the first member of the auxiliary specific binding pair and, if present, the second labeled specific binding partner that binds a molecule not cross-reactive with the analyte to the first end 24 of the first chromatographic medium 22. If analyte is present in the sample, the labeled specific binding partner to the analyte conjugated to the first member of the auxiliary specific binding pair binds to the first zone (capture zone) of immobilized analyte or analog 28 on the first chromatographic medium 22. In this case, no signal is detectable at the second zone 30 (detection zone) including the immobilized second member of the auxiliary specific binding pair bound to the first chromatographic medium 22.

In either case, whether analyte is present in the sample or not, however, the second labeled specific binding partner that binds a molecule not substantially cross-reactive with the analyte binds to the flow control zone 52 near the second end 26 of the first chromatographic medium 22 and gives a positive indication that proper flow through the first chromatographic medium has occurred.

Simultaneously, the resolubilized labeled specific binding partner to the analyte or analog thereof originally present in the comparison label zone 40 is migrating through the second chromatographic medium 32 from the first end 34 to the second end 36, and the resolubilized labeled specific binding partner to the analyte or analog thereof then binds to the immobilized analyte or analog thereof present in a predetermined quantity at the comparison zone 38 on the second chromatographic medium 32.

After a period for migration, typically 1 to 10 minutes, the user then views the second zone of immobilized analyte 30 on the first chromatographic medium 22 and the comparison zone 38 on the second chromatographic medium 32 through the aperture 42 to compare the relative intensities of the label at the zones in order to obtain a semi-quantitative estimate of the concentration of analyte in the test sample. For example, if the comparison zone 38 contains 5 ng of analyte, if the intensity present at the second zone 30 on the first chromatographic medium 22 is greater than the intensity at the comparison zone 38 on the second chromatographic medium 32, there is more than 5 ng of analyte present in the volume of the test sample applied to the assay device 10. A range of concentrations can be used.

2. Assay Device Employing Control Line Combined With Flow Indicator

Another embodiment of an assay device according to the present invention employs a combined control line and flow indicator that provide a semi-quantitative indication of the analyte in the test sample. This device also operates by a competitive immunoassay procedure.

In general, this embodiment comprises:

(1) a first opposable component including:
  (a) a sample preparation zone including:
    (i) a labeled specific binding partner for an analyte conjugated to a first member of an auxiliary specific binding pair in resolubilizable form; and
    (ii) a predetermined quantity of the analyte or an analog thereof covalently bound to a labeled specific binding partner for a molecule that does not substantially cross-react with the analyte in resolubilizable form; and
  (b) an absorber separated from the sample preparation zone; and (2) a second opposable component including a chromatographic medium with first and second ends, the chromatographic medium including thereon in discrete, nonoverlapping zones:
  (a) a first, capture, zone of immobilized analyte or analog thereof bound to the chromatographic medium;
  (b) a second, detection, zone including an immobilized molecule that is a second member of the auxiliary specific binding pair with specific affinity for the first member bound to the chromatographic medium; and
  (c) a third, control, zone including an immobilized molecule capable of being specifically bound to the labeled specific binding partner covalently conjugated to the analyte or analog thereof bound to the chromatographic medium.

Figure 2:
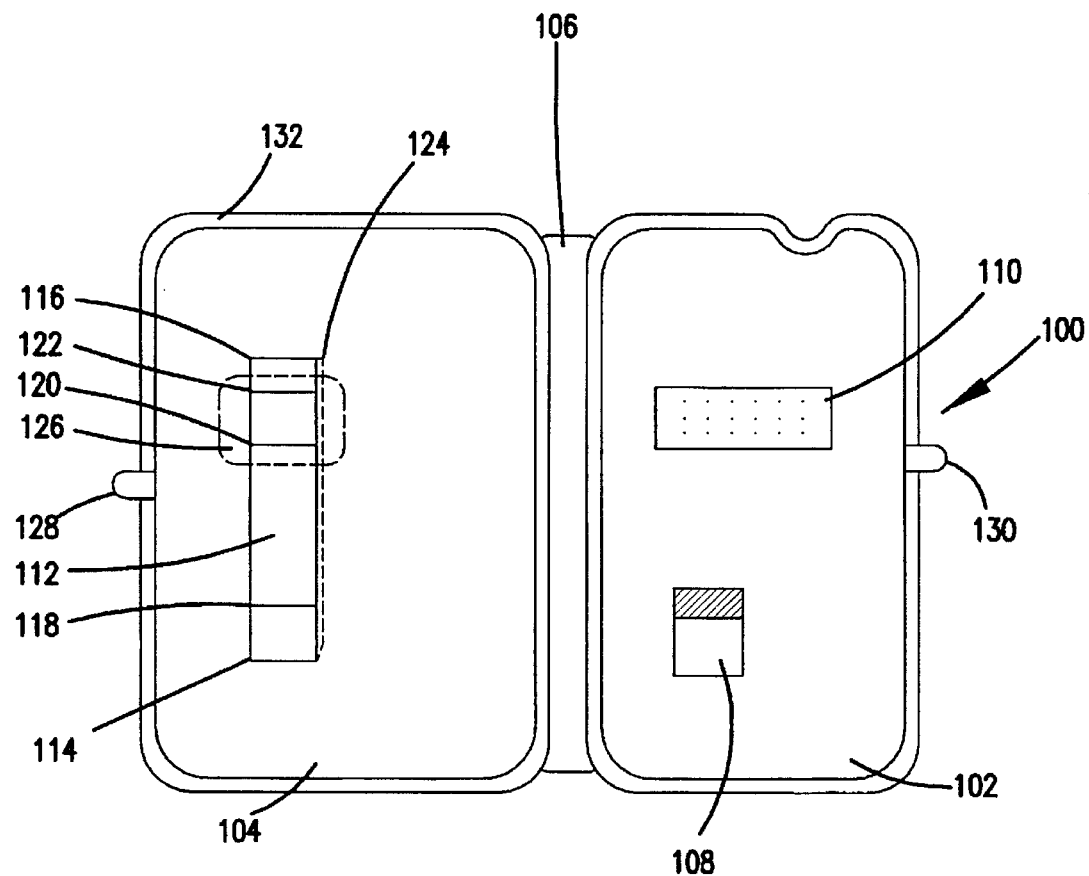
FIG. 2 is a drawing of a second embodiment of a competitive immunoassay device according to the present invention employing a single chromatographic medium.

This embodiment of the assay device is shown in FIG. 2. The assay device 100 has a first opposable component 102 and a second opposable component 104. The first and second opposable components 102 and 104 are joined by a hinge 106. The first opposable component 102 has a sample preparation zone 108. The sample preparation zone 108 includes: (1) a labeled specific binding partner for an analyte conjugated to a first member of an auxiliary specific binding pair in a form that can be resolubilized by a liquid; and (2) a predetermined quantity of the analyte or an analog thereof covalently bound to a labeled specific binding partner for a molecule that does not substantially cross-react with the analyte in a form that can be resolubilized by a liquid, typically an aqueous liquid. Typically, as described above, the first member of the auxiliary specific binding pair is biotin and the second member of the auxiliary specific binding pair is an immobilized molecule having specific binding affinity for biotin, such as avidin, streptavidin, or an anti-biotin antibody. More typically, the second member of the auxiliary specific binding pair is streptavidin. The first opposable component 102 also has an absorber 110 separated from the sample preparation zone 108 on the first opposable component 102.

The second opposable component 104 includes a chromatographic medium 112 that has a first end 114 and a second end 116. The chromatographic medium 112 includes thereon: (1) a first, capture zone 118 of immobilized analyte or analog thereof bound to the chromatographic medium 112; (2) a second, detection zone 120 including an immobilized molecule that is a second member of the auxiliary specific binding pair with specific affinity for the first member bound to the chromatographic medium 112; and (3) a third, control zone 122 including an immobilized molecule capable of being specifically bound to the labeled specific binding partner covalently conjugated to the analyte or analog thereof bound to the chromatographic medium 112. These zones are arranged so that the first, capture zone 118 is closest to the first end 114 of the chromatographic medium 112 and the third, control zone 122 is closest to the second end 116 of the chromatographic medium 112, with the second, detection zone 120 being between the first, capture zone 118 and the third, control zone 122. The chromatographic medium 112 can be backed by a plastic backing 124 as described above.

The second opposable component 104 has an aperture 126 to allow viewing of a portion of the chromatographic medium 112, the portion including the detection zone 120 and control zone 122. The first and second opposable components 102 and 104 can be held together by engagers such as locks 128 and 130. The first and second opposable components 102 and 104 can be surrounded by a gasket 132 to prevent the escape of fluids from the device.

The first and second opposable components 102 and 104 are configured so that bringing the first and second opposable components 102 and 104 into opposition from a position in which they are not in opposition causes the absorber 110 to come into operable contact with the second end 116 of the chromatographic medium 112. It also causes the sample preparation zone 108 on the first opposable component 102 to come into contact with the first end 114 of the chromatographic medium 112 so that the test sample, the resolubilized labeled specific binding partner for the analyte conjugated to the first member of the auxiliary specific binding pair, and the predetermined quantity of the analyte or analog thereof covalently bound to the labeled specific binding partner flow through the chromatographic medium 112 from the first end 114 to the second end 116.

In use, the sample is added to the sample preparation zone 108 on the first opposable component 102, to resolubilize the labeled reagents. The assay device 100 or the first opposable component 102 can be inserted into an incubator, as described above for the first embodiment. The first and second opposable components 102 and 104 are then brought into opposition, and the sample and resolubilized labeled components are allowed to migrate through the chromatographic medium 112 from the first end 114 to the second end 116.

In the absence of analyte, the labeled specific binding partner for the analyte conjugated to the first member of the auxiliary specific binding pair binds to the first, capture zone 118 of immobilized analyte or analog thereof and does not reach the second, detection zone 120 including the immobilized second member of the auxiliary specific binding pair. If, however, analyte is present in the sample, it competes for binding to the labeled specific binding partner for the analyte conjugated to biotin with the immobilized analyte or analog thereof present in the first, capture zone 118, and at least some of the labeled specific binding partner for the analyte then reaches the second, detection zone 120 including the immobilized second member of the auxiliary specific binding pair. The labeled specific binding partner for the analyte conjugated to the first member of the auxiliary specific binding pair is then bound at the second, detection zone 120, creating a detectable signal at that point. The intensity of the detectable signal is proportional to the concentration of analyte in the original test sample.

However, the control zone 122 produces a detectable signal, whether or not analyte is present in the sample, because the predetermined quantity of the analyte or analog thereof covalently bound to the labeled specific binding partner for the molecule that does not substantially cross-react with the analyte present in the sample preparation zone 108 binds to the immobilized molecule capable of being specifically bound to the labeled specific binding partner at the control zone 122. This gives a constant signal which serves both as a control zone for proper flow through the device and a comparison zone so that a quantitative determination of the analyte concentration can be obtained.

C. Multiplex Assay Devices

Although the devices described above are described in terms of devices that perform a single assay, the same principles can be used to construct multiplex assay devices capable of carrying out more than one assay at the same time. These assay devices can be constructed so that the assays that can be performed simultaneously are for the same analyte or different analytes. For example, a multiplex device according to the present invention can be used to assay a number of different analytes and different aliquots of the same sample, such as different antibiotics in different aliquots of a sample of milk, or can be used to assay the same analyte in a number of different samples. This latter mode is particularly useful in assaying for a condition for which samples taken at different times from the same patient are to be assayed for the analyte of interest. Alternatively, one or more of the assays can be used for controls or reference standards.

Multiplex devices according to the present invention can contain from 2 to 12 or more sample preparation zones and chromatographic media, depending upon the assay for which the device is to be employed. Typically, the device contains from two to five separate sample preparation zones and chromatographic media.

The principles of operation for the multiplex assay devices are exactly the same as those for the assay devices shown above in FIGS. 1 and 2, except for the performance of multiple assays on the same device.

Figure 3:
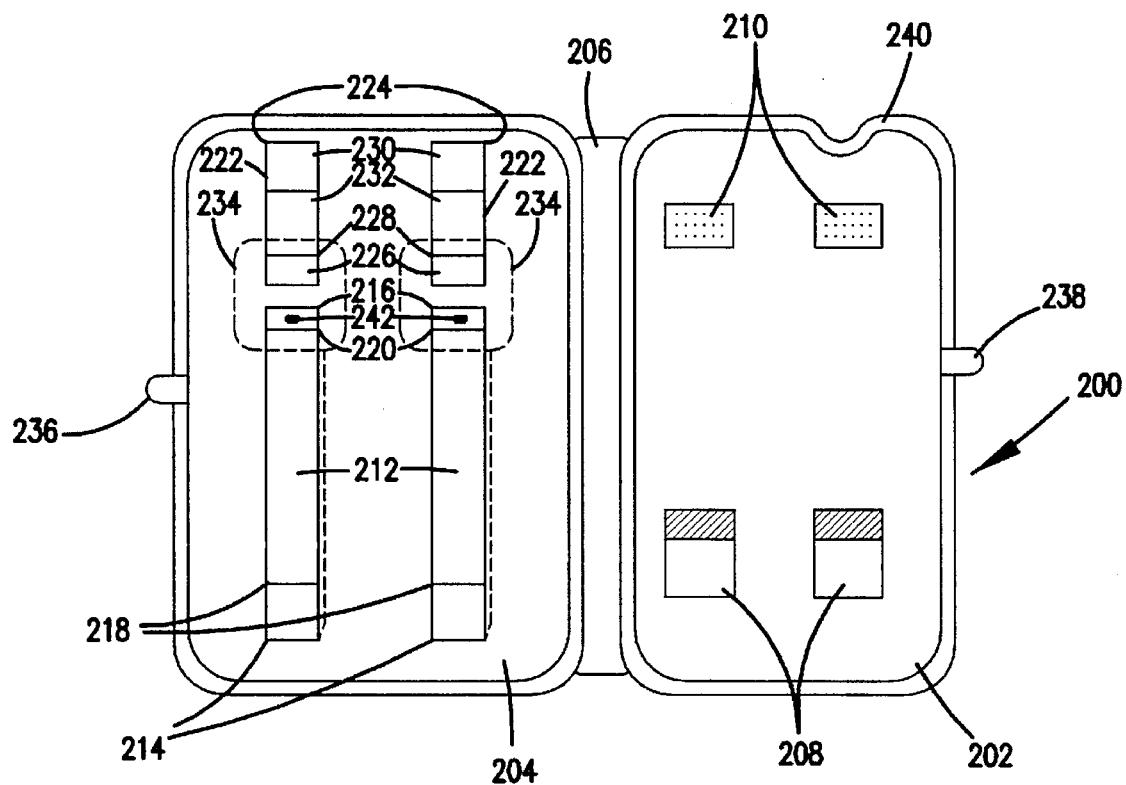
FIG. 3 is a drawing of a first embodiment of a multiplex assay device according to the present invention that operates according to the principles of the device of FIG. 1.

One embodiment of a multiplex assay device, employing the same principle as that shown in FIG. 1, is shown in FIG. 3.

In general, this device comprises:

(1) a first opposable component including:
  (a) a plurality of sample preparation zones, each sample preparation zone including a labeled specific binding partner for an analyte conjugated to a first member of an auxiliary specific binding pair in resolubilizable form; and
  (b) an absorber for absorbing fluid therein separated from the sample preparation zones on the first opposable component; and (2) a second opposable component hingedly attachable to the first opposable component including:
  (a) a plurality of first chromatographic media, one for each sample preparation zone, each first chromatographic medium having first and second ends and including thereon:
    (i) a first zone of an immobilized analyte or analog thereof bound to the first chromatographic medium; and
    (ii) a second zone of an immobilized molecule that is a second member of the auxiliary specific binding pair with specific affinity for the first member bound to the first chromatographic medium;
  (b) a plurality of second chromatographic media, one for each sample preparation zone, each second chromatographic medium having a first end and a second end and including thereon a comparison zone containing a known quantity of an analyte or analog thereof immobilized to the comparison zone; and
  (c) a plurality of comparison label zones, one for each second chromatographic medium, each comparison label zone including therein a labeled specific binding partner to the analyte or analog thereof in resolubilizable form in operable contact with the second chromatographic medium.

In this version of a multiplex assay device according to the present invention, when the first and second opposable components are brought into opposition from a position in which they are not in opposition, the sample preparation zones come into operable contact with the first end of each first chromatographic medium to apply the sample and the labeled specific binding partner for the analyte conjugated to the first member of the auxiliary specific binding pair to each first chromatographic medium, and the absorber comes into operable contact with the second end of each first chromatographic medium and the second end of each second chromatographic medium to draw fluid through the first and second chromatographic media from their first ends to their second ends. As a result, the device gives a detectable indication of the presence of an analyte in each first and second chromatographic medium at a quantity greater than a predetermined amount by a comparison of the intensity of the label bound at the detection zone of each first chromatographic medium and at the comparison zone of each second chromatographic medium.

The device 200 has a first opposable component 202 and a second opposable component 204, joined by a hinge 206.

The first opposable component 202 has a plurality of sample preparation zones 208. The first opposable component 202 has a plurality of absorbers 210, separated on the first opposable component 202 from each of the sample preparation zones 208. Alternatively, a single absorber 210 can be used, as long as there is no cross-contamination between samples.

The second opposable component 204 has a plurality of first chromatographic media 212, each with a first end 214 and a second end 216. Each first chromatographic medium 212 has a first, capture zone of immobilized analyte 218, and a second, detection zone of an immobilized molecule that is a second member of the auxiliary specific binding pair with specific affinity for the first member 220. Each second opposable component 204 also has a plurality of second chromatographic media 222, each with a first end 224 and a second end 226. Each of the second chromatographic media 222 has thereon a comparison zone 228. The second opposable component 204 has a plurality of comparison label zones 230. Each of the first and second chromatographic media 212 and 222 can be backed with a plastic backing 232. The second opposable component has one or more apertures 234 to allow viewing of the second, capture zones 220 and the comparison zones 228. The chromatographic device also has locks 236 and 238 and a gasket 240. Preferably, each first chromatographic medium 212 has a flow control indicator 242.

Figure 4:
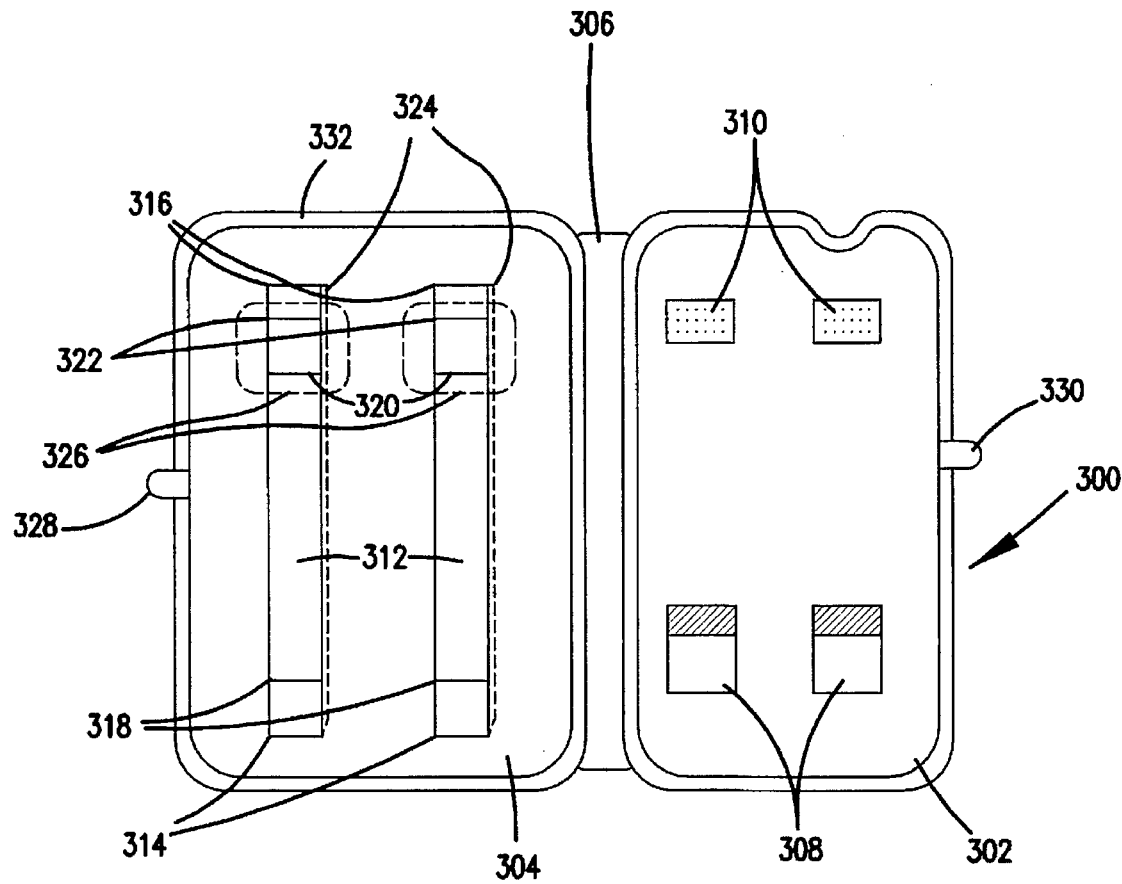
FIG. 4 is a drawing of a second embodiment of a multiplex assay device according to the present invention that operates according to the principles of the device of FIG. 2.

A multiplex assay device operating by the same principles as the assay device of FIG. 2 is shown in FIG. 4. In general, this device comprises:

(1) a first opposable component including:
   (a) a plurality of sample preparation zones, each sample preparation zone including:
       (i) a labeled specific binding partner for an analyte conjugated to a first member of an auxiliary specific binding pair in resolubilizable form; and
       (ii) a predetermined quantity of an analyte or an analog thereof covalently bound to a labeled specific binding partner for a molecule that does not substantially cross-react with the analyte in resolubilizable form; and
   (b) an absorber separated from the sample preparation zones; and
(2) a second opposable component including a plurality of chromatographic media with first and second ends, each chromatographic medium including thereon in discrete, nonoverlapping zones:
   (a) a first, capture, zone of immobilized analyte or analog thereof bound to the chromatographic medium;
   (b) a second, detection, zone including an immobilized molecule that is a second member of the auxiliary specific binding pair with specific affinity for the first member bound to the chromatographic medium; and
   (c) a third, control, zone including an immobilized molecule capable of being specifically bound to the labeled specific binding partner covalently conjugated to the analyte or analog thereof bound to the chromatographic medium.

In this version of a multiplex assay device according to the present invention, the first and second opposable components are configured so that bringing the first and second opposable components into opposition from a position in which they are not in opposition causes the absorber to come into operable contact with the second end of each chromatographic medium. This also causes the sample preparation zones to come into contact with the first end of each chromatographic medium so that the test samples, the resolubilized labeled specific binding partners for the analyte conjugated to the first member of the auxiliary specific binding partner, and the predetermined quantities of the analyte or analog thereof covalently bound to a labeled specific binding partner flow through each chromatographic medium from the first end to the second end.

The assay device 300 has a first opposable component 302 and a second opposable component 304, joined by a hinge 306. The first opposable component 302 has a plurality of sample preparation zones 308 and absorbers 310, separated from the sample preparation zones 308.

The second opposable component 304 has a plurality of chromatographic media 312, each with a first end 314 and a second end 316. Each of the chromatographic media 312 has a first, capture zone 318, a second, detection zone 320, and a third, control zone 322. Each of the chromatographic media 312 can be backed by a plastic backing 324. The second opposable component 304 has an aperture or plurality of apertures 326 to allow viewing of the detection zones 320 and control zones 322. The first and second opposable components 302 and 304 are held together by engagers such as locks 328 and 330, and are surrounded by a gasket 332 to prevent the escape of fluids.

In use, the multiplex assay devices are used exactly as the assay devices performing single assays as shown above in FIGS. 1 and 2, allowing sufficient time to allow resolubilization of the reagents on the device and migration through the chromatographic media.

II. ANALYTES AND SPECIFIC BINDING PARTNERS

A. Analytes

Typically, competitive assays such as those carried out by assay devices according to the present invention are used for monovalent analytes. The monovalent analytes are typically haptens, but the same principles can be used to assay any analyte that is monovalent, such as a normally multivalent antigen on which the additional antibody-binding sites are blocked or modified.

Assayable analytes include the following: theophylline; digoxin; disopyramide; lidocaine; procainamide; propranolol; quinidine; amikacin; penicillin and other β-lactam antibiotics including ampicillin, ampicillin derivatives, synthetic and semi-synthetic penicillins, and cephalosporins; gentamycin; kanamycin; netilmycin; tobramycin; tetracycline; sulfonamides such as phthalylsulfathiazole, sulfamethizole, sulfisoxazole, sulfamethazine, sulfisomidine, sulfacetamide, sulfanilamide, sulfaphenazole, sulfamethoxazole, sulfadiazine, sulfamethoxydiazine, sulfamethoxypyridazine, sulfadimethoxine, sulfamethoxypyrazine, sulfadoxine, and 4,4'-diaminodiphenylsulfone; tricylic antidepressants; ethosuximide; phenobarbital; diazepam; phenytoin; primidone; valproic acid; acetaminophen; acetylsalicylic acid; ibuprofen; methotrexate; drugs of abuse such as morphine, codeine, cocaine, fentanyl, 3-methylfentanyl, amphetamines, lysergic acid diethylamide, phencyclidine, N,α-dimethyl-1,3-benzodioxyl-5-ethanamine ("Ecstasy"), and heroin and their metabolites; DNP; 1-substituted-4-hydroxy-2-nitrobenzenes; 4-substituted 2-nitro-trialkylanilinium salts; and environmental contaminants such as benzene, toluene, xylene, ethylbenzene, chlordane, DDT and its metabolites, 2,4-D, 2,4,5-T, and atrazine.

Of these analytes, particularly important analytes are β-lactam antibiotics, sulfamethazine, gentamycin, and tetracycline. These antibiotics often occur in milk, and it is desirable to have a rapid method of detecting their presence in milk.

B. Specific Binding Partners

Specific binding partners suitable for performance of assays using devices according to the present invention include, but are not limited to, antibodies and specific binding proteins. An example of the latter is the penicillin binding protein (PBP) isolated from *Bacillus stearothermophilus*. Other examples of specific binding proteins are protein receptors for hormones.

Typically, antibodies against haptens are produced by immunization of an antibody-producing animal, generally a mammal such as a goat, rabbit, cow, horse, or sheep, with a hapten conjugated covalently to a carrier protein. The conjugation of a hapten to a carrier protein for antibody production is generally preferred and in some cases may be required. This is because most haptens are at most weakly immunogenic if injected into an antibody-producing animal without conjugation.

A variety of carrier proteins are well-known in the art, and can include serum albumins of various species, keyhole limpet hemocyanin, thyroglobulin, ovalbumin, fibrinogen, polylysine, and purified protein derivative of tuberculin (PPD).

A large number of coupling reagents are known in the art. Among the types of reactions used for conjugation of haptens to proteins are acylating reagents, alkylating reagents, redox reagents, and electrophilic reagents.

The choice of reaction typically depends on the groups available in the hapten for reaction. If a hapten contains a free carboxyl group or a group that can readily be carboxylated, widely used methods include the mixed anhydride method, the carbodiimide method, using carbodiimides such as 1-ethyl-3-(3-dimethylaminopropyl) carbodiimide, N,N'-dicyclohexylcarbodiimide, or 1-cyclohexyl-3(2-morpholinoethyl)carbodiimide metho-p-toluenesulfonate, and the N-hydroxysuccinimide ester procedure, in which a carbodiimide is esterified with N-hydroxysuccinimide.

Haptens with amino groups or nitro groups reducible to amino groups can be coupled to proteins through a number of reactions. If the amines are aromatic, they can be converted to diazonium salts by the slow addition of nitric acid and reacted with proteins at a moderately alkaline pH. Haptens with aliphatic amines can be conjugated to proteins by various methods, such as the use of carbodiimides, tolylene-2,4-diisocyanate, the use of maleimide compounds, or reaction with sodium periodate. Another approach is to convert aliphatic amines to aromatic amines by reacting with p-nitrobenzoylchloride and subsequently reducing to a p-aminobenzoylamide, which then can be coupled to proteins with diazotization.

Bifunctional imidate esters, which react with amino groups to form amidines, can be used to conjugate haptens to proteins. Such imidate esters include dimethyladipimidate, dimethylpimelimidate, dimethylsuberimidate, and other similar analogs.

Haptens with sulfhydryl groups can be conjugated to proteins with maleimides. Other reactions are possible, such as activation of the protein with bromoacetamide groups, or the formation of disulfide bonds between the carrier and hapten in acetate buffer, pH 4.0.

For haptens with hydroxyl groups, it is generally preferred to convert the hydroxyl to another group. For example, an alcohol can be converted to the half ester of succinic acid, which introduces a carboxyl group available for conjugation. The bifunctional reagent sebacoyldichloride converts an alcohol to an acyl chloride, which reacts readily with proteins at slightly alkaline pH. Phenols can be activated with diazotized p-aminobenzoic acid, which introduces a carboxyl group, and then can be reacted with the carrier by a mixed anhydride reaction as described above. Sugars can be activated by the formation of a p-nitrophenyl glycoside followed by the reduction of the nitro group to an amino group and conjugation after diazotization, as for aromatic amines. Another method is based on the cleavage of vicinal glycols of sugars to aldehydes, which are then coupled to amines by reductive alkylation. Also, haptens can be conjugated through chlorocarbonates, prepared with an equimolar amount of phosgene.

For haptens with aldehyde or ketone groups, carboxyl groups can be readily introduced through the formation of O-(carboxymethyl)oximes. Ketone groups can also be derivatized with p-hydrazinobenzoic acid to produce carboxyl groups which could be conjugated to the carrier as described above for carboxyl groups. Haptens containing aldehydes can be directly conjugated through the formation of Schiff bases which are stabilized by reduction with sodium borohydride.

Conjugation methods are described generally in P. Tijssen, "Practice and Theory of Enzyme Immunoassays", (Elsevier, Amsterdam, 1985), ch. 12, pp. 279–296. Other conjugation methods are known in the art and can be used for particular haptens.

III. TEST KITS

Another aspect of the present invention is test kits for performance of assays using assay devices according to the present invention. These test kits incorporate an assay device of the embodiment described above in Section I(B)(1), with two chromatographic media.

Test kits according to the present invention can comprise:
(1) the immunoassay device; and
  (b) a liquid for resolubilizing the labeled specific binding partner to the analyte or analog thereof in the comparison label zone.

The liquid is typically an aqueous liquid. The aqueous liquid is typically water, saline, or a buffered solution, but other aqueous liquids can be used. The immunoassay device in the test kit can be either an assay device that performs a single assay or a multiplex assay device. If the immunoassay device is a multiplex assay device, the kit typically includes enough liquid for resolubilizing the labeled specific binding partner to the analyte or analog thereof in each comparison label zone.

Test kits according to the present invention can also contain other reagents, such as reagents to extract or treat the sample.

EXAMPLES

The invention is illustrated by the following Examples. These Examples are for illustrative purposes only and are not to be construed as limiting the scope of the invention in any manner.

Example 1

Assay Device for Detection of β-Lactam Antibiotics in Milk (Prospective Example)

The assay device described in this example is intended for the detection of β-lactam antibiotics (penicillins, ampicillin, or cephalosporins) in milk. It can be used for other assays as well.

This device is constructed according to FIG. 1. The first opposable component 10 and the second opposable component 12 are solid bleached sulfite. The first opposable component 12 comprises a sample preparation zone 18 made of Cytosep (Ahlstrom Filtration, Holly Springs, Pa.). The sample preparation zone includes penicillin binding protein conjugated to biotin and labeled with colloidal gold. The sample preparation zone 18 further includes 10% anti-rabbit immunoglobulin G from an animal such as sheep or goat. The biotin-labeled penicillin binding protein and anti-rabbit immunoglobulin G were separately mixed with equal volumes of conjugate diluent (5 mM borate, 0.1% Triton X-100, 1% bovine serum albumin, 5% sucrose, pH 8.0) and are dried at 37° C. for 30 minutes.

The second opposable component 14 includes a first chromatographic medium 22 of 20 μM nitrocellulose (Schleicher & Schuell (Keene, N.H.)). The first chromatographic medium 22 has bound thereon at a first zone 28 7-aminocephalosporanic acid conjugated to goat immunoglobulin G and dried on the first chromatographic medium from conjugate diluent as described above. Typically, the chromatographic medium has dimensions of about 0.5 inch to about 1 inch for its length and of about 0.125 inch to about 0.375 inch for its width. The first chromatographic medium also has a second zone 30 of streptavidin bound to the first chromatographic medium 22. The streptavidin is dissolved in conjugate diluent and dried down as above. The first chromatographic medium 22 further includes a flow control indicator 52 which is rabbit immunoglobulin G dissolved in conjugate buffer and dried down. The first chromatographic medium 22 is backed by a polycarbonate test strip backing (Lexan) 42.

The first chromatographic medium 22 also includes a flow control indicator 52, which is rabbit immunoglobulin G dried down from conjugate diluent as described above. The second chromatographic medium 32 is made of 20 micron nitrocellulose (Schleicher & Schuell). The dimensions of the second chromatographic medium are typically the same as those of the first chromatographic medium. The second chromatographic medium 32 includes thereon 5 ng penicillin G immobilized on the chromatographic medium through a protein carrier, such as keyhole limpet hemocyanin (KLH). The second chromatographic medium 32 further includes gold-labeled penicillin binding protein as the comparison label zone 40.

In use, a raw milk sample is added to the sample preparation zone 18. The first opposable component 12 can be slid into an incubator. After the incubation step, 2 drops of reagent A (0.005M phosphate buffered saline, 0.4% Tween 20, 1.25 mM HEPES, 0.0025% Triton X-100, 0.0015% EDTA, 0.25% sodium azide, pH 7.5) is added to the comparison label zone 40 on the second opposable component 32. The device is then closed and the results read. If the test line is less intense than the control line, the milk sample contains less than 5 ng of penicillin G or equivalent. Conversely, if the test line is more intense than the control line, the sample contains more than 5 ng of penicillin G. Color always appears at the flow control area provided proper flow has occurred.

Example 2

Test Device for Detection of Gentamycin, Sulfamethazine or Tetracycline in Milk (Prospective Example)

A device for the detection of one of the antibiotics gentamycin, sulfamethazine, or tetracycline in milk is constructed according to Example 1, except that the gold-labeled penicillin binding protein conjugated to biotin on the sample preparation zone 18 of the first opposable component 12 is replaced with a monoclonal antibody for the antibiotic conjugated to biotin and labeled with colloidal gold. Similarly, the comparison label zone is the same monoclonal antibody labeled with colloidal gold. The first zone 28 of immobilized antigen or analog thereof bound to the first chromatographic medium 22 is the antigen covalently bound to an immunoglobulin G species that is not specifically bound by anti-rabbit immunoglobulin G antibody. The control line is 5 ng of the antigen or an equivalent immobilized on the second chromatographic medium 32.

Other details of construction and performance of the assay are as in Example 1.

Example 3

Test Device for Detection of β-Lactam Antibiotics in Milk (Alternative Format)

(Prospective Example)

A test device for the detection of β-lactam antibiotics in milk can be constructed in the alternative format of FIG. 2. This device is constructed according to FIG. 2. The first and second opposable components 102 and 104 are solid bleached sulfite. The sample preparation zone 108 includes 5 ng/ml penicillin G (or equivalent) bound to colloidal gold via anti-rabbit immunoglobulin G. The sample preparation zone 108 also includes biotin-labeled penicillin binding protein labeled with colloidal gold. These reagents are dried down on the sample preparation zone, which is Cytosep (Ahlstrom), as above. The absorber 110 is Ahlstrom 270.

The second opposable component 104 has a chromatographic medium 112 that is 20-micron nitrocellulose (Schleicher & Schuell). The chromatographic medium 112 is backed by a Lexan backing. The chromatographic medium 112 includes thereon: (1) the first capture zone 118 of 7-aminocephalosporanic acid conjugated to goat immunoglobulin G and immobilized on the chromatographic medium; (2) a detection zone 120 of streptavidin as in Example 1; and (3) a control zone 122, which also serves as a flow indicator, which is immobilized rabbit immunoglobulin G. In use, a raw milk sample is added to the sample preparation zone 108, and the test card is slid into an incubator as for Example 1. The device is then closed and the results are read. If the test line is less intense than the control line, the milk sample contains less than 5 ng of penicillin G or equivalent. Conversely, if the test line is more intense than the control line, the sample contains more than 5 ng of penicillin G. In each case, the control line, which also serves as the flow indicator, should give a detectable signal.

Example 4

Assay Device for Detection of Gentamycin, Sulfamethazine, or Tetracycline in Milk (Alternative Format)

(Prospective Example)

A device for the detection of gentamycin, sulfamethazine, or tetracycline in milk, in the alternative format, is constructed according to Example 3, except that the sample preparation zone 108 on the first opposable component 102 has 5 ng of antibiotic (or equivalent) covalently bound to anti-rabbit immunoglobulin G bound to colloidal gold, as well as a monoclonal antibody to the antigen (see Example 2) labeled with colloidal gold and bound to biotin.

The capture zone 118 on the chromatographic medium 112 is the antigen covalently bound to goat immunoglobulin G. Other details of construction and performance of the assay are as in Example 3.

ADVANTAGES OF THE INVENTION

Chromatographic assay devices according to the present invention can perform semiquantitative assays for a wide variety of antigens and haptens while providing a positive indication of correct performance of the assay.

Chromatographic assay devices according to the present invention also provide an advantage in being constructed of opposable elements. The use of opposable elements provides great versatility, as it permits the performance of reactions in a number of different sequences. This is possible because the use of such opposable elements allows the delivery of reagents to precisely defined regions of a test strip or other reaction component. The use of opposable elements also provides optimum performance with minimum consumption of reagents by ensuring that reagents are not wasted by being sequestered in dead volumes of apparatus. Finally, the use of opposable components provides optimum containment of possibly contaminated blood samples, each as those containing HIV or hepatitis virus.

The use of opposable elements that can be brought into opposition by direct manual closure allows the operator to perform assays according to the present invention without the use of additional liquids or breakable capsules. This allows the performance of assays without the addition of additional liquid once the sample or samples are applied to the chromatographic medium, avoiding dilution and preserving the sensitivity of assays performed with assay devices according to the present invention.

Additionally, chromatographic assay devices according to the present invention allow the rapid and accurate detection of clinically important analytes. The construction of the devices allows more even application of the samples to the chromatographic medium, and reduces interference that might otherwise be introduced by particulates or colored samples. The use of colloidal metal labels in a resolubilizable form provides extremely rapid kinetics of labeling and improves the performance of the assay.

Test methods using devices according to the present invention have a wide dynamic range and are substantially free from false negatives that may occur in other test methods at high concentrations of analyte.

Although the present invention has been described with considerable detail, with reference to certain preferred versions thereof, other versions and embodiments are possible. These versions include other arrangements of two-component devices that operate by the basic principles described herein and perform competitive immunoassays. Therefore, the scope of the invention is determined by the following claims.

I claim:

1. A competitive immunoassay device comprising:
   (a) a first opposable component including:
      (i) a sample preparation zone including a labeled specific binding partner for an analyte conjugated to a first member of an auxiliary specific binding pair in resolubilizable form; and
      (ii) an absorber for absorbing fluid therein separated from the sample preparation zone on the first opposable component; and
   (b) a second opposable component hingedly attached to the first opposable component including:
      (i) a first chromatographic medium having first and second ends and including thereon:
         (A) a first zone of immobilized analyte or analog thereof located closer to the first end of the chromatographic medium than to the second end of the chromatographic medium; and
         (B) a second zone of an immobilized molecule which is a second member of the auxiliary specific binding pair with specific affinity for the first member located closer to the second end of the first chromatographic medium than to the first end of the first chromatographic medium;
      (ii) a second chromatographic medium having a first end and a second end and including thereon a comparison zone containing a known quantity of the analyte or analog thereof immobilized to the comparison zone, the second chromatographic medium being separated from the first chromatographic medium on the first opposable component; and
      (iii) a comparison label zone distinct from the comparison zone and separated from the first and second chromatographic medium including therein a labeled specific binding partner to the analyte or analog thereof in resolubilizable form in operable contact with the second chromatographic medium;
   wherein when the first and second opposable components are brought into opposition from a position in which they are not in opposition, the sample preparation zone comes into operable contact with the first end of the first chromatographic medium to apply the sample and the labeled specific binding partner for the analyte conjugated to the first member of the auxiliary specific binding pair to the first chromatographic medium, and the absorber comes into operable contact with the second end of the first chromatographic medium and the second end of the second chromatographic medium to draw fluid through the first and second chromatographic medium from their first end to their second end so that the device gives a detectable comparative indication of the presence of an analyte.

2. The immunoassay device of claim 1 wherein the sample preparation zone on the first opposable component further includes a second labeled specific binding partner that binds a molecule not cross-reactive with the analyte in resolubilizable form, and the first chromatographic medium further includes a flow control indicator located near the second end of the first chromatographic medium including an immobilized molecule binding the second labeled specific binding partner so that the flow control indicator gives a positive indication that flow has occurred through the first chromatographic medium.

3. The immunoassay device of claim 1 wherein the label of both the labeled specific binding partner for the analyte conjugated to the first member of the auxiliary specific binding pair and the labeled specific binding partner to the analyte in the comparison label zone are visibly detectable labels.

4. The immunoassay device of claim 3 wherein the labeled specific binding partner to the analyte conjugated to the first member of the auxiliary specific binding pair at the sample preparation zone and the labeled specific binding partner to the analyte at the comparison label zone are the same label.

5. The immunoassay device of claim 1 wherein the first member of the auxiliary specific binding pair is biotin.

6. The immunoassay device of claim 5 wherein the second member of the auxiliary specific binding pair is streptavidin.

7. The immunoassay device of claim 6 wherein the analyte is a β-lactam antibiotic, the first zone of immobilized analyte or analog thereof is 7-aminocephalosporanic acid conjugated to immunoglobulin, and the labeled specific binding partner for the analyte conjugated to biotin is biotinylated penicillin binding protein.

8. The immunoassay device of claim 6 wherein the analyte is an antibiotic selected from the group consisting of gentamycin, sulfamethazine, and tetracycline, the first zone of immobilized analyte or analog thereof is analyte covalently conjugated to immunoglobulin, and the labeled specific binding partner for the analyte conjugated to biotin is a biotinylated anti-analyte antibody.

9. A test kit for detection and/or determination of an analyte comprising, packaged in separate containers:
   (a) the immunoassay device of claim 1; and
   (b) a liquid for resolubilizing the labeled specific binding partner to the analyte or analog thereof in the comparison label zone.

10. A method for detecting and/or determining an analyte in a test sample by a competitive immunoassay comprising the steps of:
   (a) adding a test sample to the sample preparation zone of the competitive immunoassay device of claim 1;
   (b) allowing the test sample to resolubilize the labeled specific binding partner for the analyte conjugated to the first member of the auxiliary specific binding pair;
   (c) adding a liquid to the comparison label zone to resolubilize the labeled specific binding partner to the analyte or analog thereof;
   (d) bringing the first and second opposable components into opposition from a position in which they are not in opposition to bring the absorber on the first opposable component into operable contact with the second end of the first chromatographic medium and the second end of the second chromatographic medium and to bring the sample preparation zone into operable contact with the first end of the first chromatographic medium;
   (e) allowing the sample and the labeled specific binding partner for the analyte conjugated to the first member of the auxiliary specific binding pair to flow through the first chromatographic medium and allowing the labeled specific binding partner to the analyte or analog thereof to flow through the second chromatographic medium so that, if analyte is present in the test sample, the labeled specific binding partner to the analyte conjugated to the first member of the auxiliary specific binding pair binds to the second zone containing the immobilized molecule that is the second member of the auxiliary specific binding pair on the first chromatographic medium and so that the labeled specific binding partner to the analyte or analog thereof binds to the comparison zone on the second chromatographic medium; and
   (f) comparing the intensity of label at the second zone on the first chromatographic medium containing the immobilized molecule that is the second member of the auxiliary specific binding pair and at the comparison zone on the second chromatographic medium to detect and/or determine the analyte in the test sample.

11. A competitive immunoassay device comprising:
   (a) a first opposable component including:
      (i) a sample preparation zone including:
         (A) a labeled specific binding partner for an analyte conjugated to a first member of an auxiliary specific binding pair in resolubilizable form; and
         (B) a predetermined quantity of the analyte or an analog thereof covalently bound to a labeled specific binding partner for a molecule that does not cross-react with the analyte in resolubilizable form; and
      (ii) an absorber separated from the sample preparation zone; and
   (b) a second opposable component including a chromatographic medium with first and second ends, the chromatographic medium including thereon in discrete, nonoverlapping zones:
      (i) a first capture zone of immobilized analyte or analog thereof;
      (ii) a second detection zone, including an immobilized molecule that is a second member of the auxiliary specific binding pair with specific affinity for the first member; and
      (iii) a third control zone, including an immobilized molecule capable of being specifically bound to the labeled specific binding partner covalently conjugated to the analyte or analog thereof located in the sample preparation zone on the first opposable component, the first, capture zone being located closer to the first end of the chromatographic medium than to the second end of the chromatographic medium, the third, control zone being located closer to the second end of the chromatographic medium than to the first end of the chromatographic medium, and the second, detection zone being located between the first capture zone and the third control zone;

wherein the first and second opposable components are configured so that bringing the first and second opposable components into opposition from a position in which they are not in opposition causes the absorber to come into operable contact with the second end of the chromatographic medium and causes the sample preparation zone to come into contact with the first end of the chromatographic medium so that the test sample, the resolubilized labeled specific binding partner for the analyte conjugated to the first member of the auxiliary specific binding pair, and the predetermined quantity of the analyte or analog thereof covalently bound to the labeled specific binding partner flow through the chromatographic medium from the first end to the second end so that the device gives a detectable comparative indication of the presence of the analyte.

12. The immunoassay device of claim 11 wherein the label of the labeled specific binding partner for the analyte conjugated to the first member of the auxiliary specific binding pair and the label of the labeled specific binding partner for the molecule that does not cross-react with the analyte are both visually detectable labels.

13. The immunoassay device of claim 11 wherein the first member of the auxiliary specific binding pair is biotin.

14. The immunoassay device of claim 13 wherein the second member of the auxiliary specific binding pair is streptavidin.

15. The immunoassay device of claim 14 wherein the analyte is a β-lactam antibiotic, the labeled specific binding partner for the analyte conjugated to biotin is a penicillin binding protein, the immobilized analyte or analog thereof bound at the capture zone on the chromatographic medium is 7-aminocephalosporanic acid covalently conjugated to immunoglobulin G, the labeled specific binding partner for a molecule that does not cross-react with the analyte is an anti-rabbit immunoglobulin G antibody, and the immobilized molecule bound at the control zone on the chromatographic medium is rabbit immunoglobulin G.

16. The immunoassay device of claim 14 wherein the analyte is an antibiotic selected from the group consisting of gentamycin, sulfamethazine, and tetracycline, the labeled specific binding partner for the analyte conjugated to biotin is an anti-analyte antibody, the labeled specific binding partner for a molecule that does not cross-react with the analyte is anti-rabbit immunoglobulin G, the immobilized analyte or analog thereof bound at the capture zone on the chromatographic medium is the analyte covalently bound to immunoglobulin G of a species other than the species other than rabbit, and the immobilized molecule bound at the control zone is rabbit immunoglobulin G.

17. A method for detecting and/or determining an analyte in a test sample by a competitive immunoassay comprising the steps of:

(a) applying the sample to the sample preparation zone of the competitive immunoassay device of claim 11;

(b) allowing the sample applied to the sample preparation zone to resolubilize the labeled specific binding partner for the analyte conjugated to the first member of the auxiliary specific binding pair and the predetermined quantity of the analyte or analog thereof covalently bound to the labeled specific binding partner for the molecule that does not cross-react with the analyte;

(c) bringing the first and second opposable components into opposition from a position in which they are not in opposition so that the absorber is brought into operable contact with the second end of the chromatographic medium and so that the sample preparation zone is brought into operable contact with the first end of the chromatographic medium;

(d) allowing the sample, the labeled specific binding partner for the sample, and the analyte or analog thereof covalently bound to the labeled specific binding partner for the molecule that does not cross-react with the analyte to migrate through at least a portion of the chromatographic medium including the detection zone and the control zone; and (e) detecting and/or determining the concentration of analyte in the test sample by comparing the intensities of label at the detection zone and the control zone of the chromatographic medium.

18. A competitive immunoassay device comprising:

(a) a first opposable component including:

(i) a plurality of sample preparation zones, each sample preparation zone including a labeled specific binding partner for an analyte conjugated to a first member of an auxiliary specific binding pair in resolubilizable form; and (ii) an absorber for absorbing fluid therein separated from the sample preparation zones on the first opposable component; and (b) a second opposable component hingedly attachable to the first opposable component including:

(i) a plurality of first chromatographic media, one for each sample preparation zone, each first chromatographic medium having first and second ends and including thereon:

(A) a first zone of an immobilized analyte or analog thereof located closer to the first end of the first chromatographic medium than to the second end of the first chromatographic medium;

(B) a second zone of an immobilized molecule that is a second member of the auxiliary specific binding pair with specific affinity for the first member located closer to the second end of the first chromatographic medium than to the first end of the first chromatographic medium;

(ii) a plurality of second chromatographic media, separated from the first chromatographic media on the second opposable component, one for each sample preparation zone, each second chromatographic medium having a first end and a second end and including thereon a comparison zone containing a known quantity of an analyte or analog thereof immobilized to the comparison zone; and (iii) a plurality of comparison labeled zones, distinct from the comparison zones and separated from the first and second chromatographic media, one for each second chromatographic medium, each comparison labeled zone including therein a labeled specific binding partner to the analyte or analog thereof in resolubilizable form in operable contact with the second chromatographic medium;

wherein, when the first and second opposable components are brought into opposition from a position in which they are not in opposition, the sample preparation zones come into operable contact with the first end of each first chromatographic medium to apply the sample and the labeled specific binding partner for the analyte conjugated to the first member of the auxiliary specific binding pair to each first chromatographic medium, and the absorber comes into operable contact with the second end of each first chromatographic medium and the second end of each second chromatographic medium to draw fluid through the first and second chromatographic media from their first ends to their second ends so that the device gives a detectable comparative indication of the presence of an analyte in at least one first and second chromatographic medium.

19. The immunoassay device of claim 18 wherein the sample preparation zones on the first opposable component further each include a second labeled specific binding partner that binds a molecule not cross-reactive with the analyte in resolubilizable form, and each first chromatographic medium further includes a flow control indicator including a molecule binding each second labeled specific binding partner so that each flow control indicator gives a positive indication that flow has occurred through each first chromatographic medium.

20. The immunoassay device of claim 18 wherein the first member of the auxiliary specific binding pair is biotin.

21. The immunoassay device of claim 18 wherein the second member of the auxiliary specific binding pair is streptavidin.

22. A test kit for detection and/or determination of at least one analyte comprising, packaged in separate containers:

(a) the immunoassay device of claim 18; and (b) a liquid for resolubilizing the labeled specific binding partner to the analyte or analog thereof in each comparison label zone.

23. A method for detecting and/or determining at least one analyte in at least one test sample by a competitive immunoassay comprising the steps of:

(a) adding a test sample to at least one of the sample preparation zones of the competitive immunoassay device of claim 18;

(b) allowing the at least one test sample to resolubilize the labeled specific binding partners for the analyte conjugated to the first member of the auxiliary specific binding partner;

(c) adding a liquid to at least one of the comparison label zones to resolubilize the labeled specific binding partner to the analyte or analog thereof;

(d) bringing the first and second opposable components into opposition from a position in which they are not in opposition to bring the absorber on the first opposable component into operable contact with the second end of the first chromatographic media and the second end of the second chromatographic media and to bring the sample preparation zones into operable contact with the first ends of the first chromatographic media;

(e) allowing the at least one sample and the labeled specific binding partner for the analyte conjugated to the first member of the auxiliary specific binding pair to flow through the first chromatographic media and the labeled specific binding partner to the analyte or analog thereof to flow through the second chromatographic media so that, if analyte is present in any test sample, the labeled specific binding partner to the analyte conjugated to biotin binds to the detection zone on the corresponding first chromatographic medium and so that the labeled specific binding partner binds to the comparison zone on the corresponding second chromatographic medium; and (f) comparing the intensity of label at the detection zone on each first chromatographic medium and at the comparison zone on each second chromatographic medium to detect and/or determine the analyte in each test sample.

24. A competitive immunoassay device comprising:
(a) a first opposable component including:
  (i) a plurality of sample preparation zones, each sample preparation zone including:
    (A) a labeled specific binding partner for an analyte conjugated to a first member of an auxiliary specific binding pair in resolubilizable form; and
    (B) a predetermined quantity of an analyte or analog thereof covalently bound to a labeled specific binding partner for a molecule that does not cross-react with the analyte in resolubilizable form; and
  (ii) an absorber separated from the sample preparation zone; and
(b) a second opposable component including a plurality of chromatographic media each with first and second ends, each chromatographic medium including thereon in discrete, nonoverlapping zones:
  (i) a first capture zone of immobilized analyte or analog thereof;
  (ii) a second detection zone, including an immobilized molecule that is a second member of the auxiliary specific binding pair with specific affinity for the first member; and (iii) a third control zone including an immobilized molecule capable of being specifically bound to the labeled specific binding partner covalently conjugated to the analyte or analog thereof, the first capture zone being located closer to the first end of the chromatographic medium than to the second end of the chromatographic medium, the third, control zone, being located closer to the second end of the chromatographic medium than to the first end of the chromatographic medium, and the second detection zone being located between the first and third zones;

wherein the first and second opposable components are configured so that bringing the first and second opposable components into opposition from a position in which they are not in opposition causes the absorber to come into operable contact with the second end of each chromatographic medium and causes the sample preparation zones to come into contact with the first end of each chromatographic medium so that the test samples, the resolubilized labeled specific binding partners for the analyte conjugated to the first member of the auxiliary specific binding pair, and the predetermined quantities of the analyte or analog thereof covalently bound to a labeled specific binding partner flow through each chromatographic medium from the first end to the second end so that the device gives a detectable comparative indication of the presence of an analyte in at least one chromatographic medium.

25. The immunoassay device of claim 24 wherein the label of the labeled specific binding partner for each analyte conjugated to the first member of the auxiliary specific binding pair and the label of each labeled specific binding partner for the molecule that does not cross-react with the analyte are both visually detectable labels.

26. The immunoassay device of claim 24 wherein the first member of the auxiliary specific binding pair is biotin.

27. The immunoassay device of claim 26 wherein the second member of the auxiliary specific binding pair is avidin.

28. A method for detecting and/or determining at least one analyte in at least one test sample by a competitive immunoassay comprising the steps of:
(a) applying a sample to at least one of the sample preparation zones of the competitive immunoassay device of claim 24;
(b) allowing the at least one sample applied to the sample preparation zones to resolubilize the labeled specific binding partner for the analyte conjugated to the first member of the auxiliary specific binding pair and the predetermined quantity of the analyte or analog thereof covalently bound to the labeled specific binding partner for the molecule that does not cross-react with the analyte;
(c) bringing the first and second opposable components into opposition from a position in which they are not in opposition so that the absorber is brought into operable contact with the second end of each chromatographic medium and so that each sample preparation zone is brought into operable contact with the first end of each chromatographic medium;
(d) allowing the at least one sample, the labeled specific binding partner for the sample, and the analyte or analog thereof covalently bound to the labeled specific binding partner for the molecule that does not cross-react with the analyte to migrate through at least a portion of each chromatographic medium including the detection zone and the control zone; and
(e) detecting and/or determining the concentration of analyte in each test sample by comparing the intensities of label at the detection zone and the control zone of each chromatographic medium.

* * * * *